United States Patent
Hirahara (12)

(10) Patent No.: US 6,684,564 B1
(45) Date of Patent: Feb. 3, 2004

(54) EMBRYO DELIVERY SYSTEM FOR MANUFACTURED SEEDS

(75) Inventor: Edwin Hirahara, Chehalis, WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

(21) Appl. No.: 09/644,200

(22) Filed: Aug. 22, 2000

Related U.S. Application Data

(60) Provisional application No. 60/150,292, filed on Aug. 23, 1999.

(51) Int. Cl.[7] ............................. A10C 1/06; A10C 21/00
(52) U.S. Cl. ................ 47/57.6; 47/58.15 E; 47/DIG. 9; 71/5; 428/15; 428/403
(58) Field of Search ................................. 47/57.6, 58.1, 47/DIG. 9; 71/5; 428/15, 403; A01C 01/06

(56) References Cited

U.S. PATENT DOCUMENTS

| | | | |
|---|---|---|---|
| 4,777,907 A | | 10/1988 | Sänger |
| 5,284,765 A | * | 2/1994 | Bryan et al. ............... 435/240.4 |
| 5,877,850 A | * | 3/1999 | Ogata ......................... 356/3.04 |
| 6,145,247 A | * | 11/2000 | McKinnis .................... 47/57.6 |

FOREIGN PATENT DOCUMENTS

| | | | | |
|---|---|---|---|---|
| DE | 2 139 567 | | 3/1973 | |
| EP | 0776601 A1 | * | 6/1997 | ............ A01C/1/06 |
| GB | 1 507 365 | | 4/1978 | |
| WO | WO 91/00781 | | 1/1991 | |
| WO | WO-9100781 | * | 1/1991 | ............ B07C/5/34 |
| WO | WO 95/05064 | | 2/1995 | |

OTHER PUBLICATIONS

Win/MacSeedle, Regent Instruments Inc., Image Analysis systems and Software, Jul. 1998, www.regent.qc.ca/products/products.html. 12 pages.*

Grob, J.A., et al. "Dimensional Model of Zygotic Douglas-–Fir Embryo Development," *International Journal of Plant Sciences 160* (4):653–662, 1999.

Timmis, R., "Bioprocessing for Tree Production in the Forest Industry: Conifer Somatic Embryogenesis," *Biotechnology Progress 14*(1):156–166, Feb. 1998.

* cited by examiner

*Primary Examiner*—Peter M. Poon
*Assistant Examiner*—Andrea M. Valenti
(74) *Attorney, Agent, or Firm*—Christensen O'Connor Johnson Kindness PLLC

(57) ABSTRACT

A method of delivering cultivated plant embryos including the step of orientating a plurality of plant embryos in a predetermined orientation. Analyzing each of the plurality of embryos according to a predetermined quality criteria to identify qualified embryos. Determining positional measurements of the qualified embryos and positioning a first seed coat relative to the qualified embryos. The method also includes the step of inserting one of the qualified embryos in the seed coat according to the positional measurements of the qualified embryos to minimize damage to and contamination of the qualified embryos.

46 Claims, 5 Drawing Sheets

EMBRYO DELIVERY SYSTEM FOR MANUFACTURED SEEDS

RELATED APPLICATION

The present invention claims the benefit of U.S. provisional patent application serial No. 60/150,292, filed Aug. 23, 1999.

FIELD OF THE INVENTION

The present invention relates generally to manufactured seeds and, more particularly, to a system for the delivery of plant embryos to various growing platforms.

BACKGROUND OF THE INVENTION

Modern agriculture, including silviculture, often requires the planting of large numbers of substantially identical plants genetically tailored to grow optimally in a particular locale or to possess certain other desirable traits. Production of new plants by sexual reproduction can be slow and is often subject to genetic recombinational events resulting in variable traits in its progeny. As a result, asexual propagation has been shown for some species to yield large numbers of genetically identical embryos, each having the capacity to develop into a normal plant. Such embryos must usually be further cultured under laboratory conditions until they reach an autotrophic "seedling" state characterized by an ability to produce their own food via photosynthesis, resist desiccation, produce roots able to penetrate soil and fend off soil microorganisms.

Some researchers have experimented with the production of artificial seeds, known as manufactured seeds, in which individual plant somatic or zygotic embryos are encapsulated in a seed coat, such as those disclosed in U.S. Pat. No. 5,701,699, issued to Carlson et al., the disclosure of which is hereby expressly incorporated by reference.

Typical manufactured seeds include a seed coat, a synthetic gametophyte and a plant embryo. The seed coat is usually a capsule having a closed end and an open end. The synthetic gametophyte is placed within the seed coat, such that it substantially fills the seed coat. A cotyledon restraint may be centrally located within the synthetic gametophyte. The cotyledon restraint includes a centrally located cavity extending partially through its the length and is sized to receive the plant embryo therein. The well known plant embryo includes a radicle end and a cotyledon end. The plant embryo is deposited within the cavity of the cotyledon restraint cotyledon end first. The plant embryo is typically sealed within the seed coat by at least one end seal.

In the past, delivery of the plant embryo within the seed coat has utilized a liquid-based transport system to move the plant embryo through the manufactured seed production line. In such a liquid-based transport system, plant embryos are placed in a container of liquid to orient them in a like direction. The plant embryos are caused to float to the top of the container, such that each embryo floats upwardly within the container cotyledon end first. From the top of the container, additional liquid is used to propel the plant embryos out of the container while maintaining their cotyledon end first orientation. Liquid is then used to transport the plant embryos through the remaining manufactured seed production line steps. Although such liquid-based plant embryo delivery systems are effective at transporting plant embryos, they are not without their problems.

First, both system response and plant embryo movements through the system are slow because electromechanical actuators are required for controlling the liquid flow. Second, handling of the plant embryo is not precise. Often it is difficult to manipulate a plant embryo suspended in liquid, as it is difficult to manipulate any objects suspended in liquid. Third, it is difficult to reliably detect plant embryos because of their small size, the requirement for a large diameter transport tube, and cavitation in the liquid. Additionally, it is difficult to analyze each plant embryo for quality when it is suspended in liquid. Further, removing all of the liquid after the plant embryo is placed in the cavity of the cotyledon restraint is difficult. Removing all of the liquid from the embryo is desirable because liquid may cause early germination or rot. Slow throughput of the liquid system requires multiple liquid systems to meet the overall production quantity goals. Finally, the large numbers of components in a liquid delivery system present reliability problems, as well as difficulties in maintaining the system.

Thus, there exists a need for a plant embryo delivery system that is capable of reliably producing a large number of manufactured seeds at a relatively low cost, and minimizing the risk of damaging or contaminating the plant embryo.

SUMMARY OF THE INVENTION

In accordance with one embodiment of the present invention, a method of delivering cultivated plant embryos is provided. The method includes the step of orientating a plurality of embryos in a predetermined orientation. The method also includes analyzing each of the plurality of embryos according to a predetermined quality criteria to identify qualified plant embryos. Further, the steps of determining the positional measurements of the qualified embryos, and positioning a first seed coat relative to the qualified embryos are also included in the method of the present invention. The method further includes the step of inserting one of the qualified embryos in the seed coat according to the positional measurements of the qualified embryos to minimize damage to and contamination of the qualified embryos.

The method of delivering a plant embryo of the present invention has several advantages over currently available plant embryo delivery systems. The delivery system of the present invention uses mini-robotic pick and place systems with motion control to increase the speed and accuracy of the embryo delivery system. Embryo manipulation is transformed from a non-precise environment to a precise environment at the front end of the embryo processing on the manufacturing line. In a robotics system, precise information about an object and the ability to move that object with precision allows the opportunity to move the object faster. The overall system is simpler because it utilizes computerized electronics and machine control equipment. Using less components and, therefore, less equipment results in a more reliable system. Further, liquid is removed from around the embryo as one of the first process steps, thereby eliminating the potential for liquid contamination of the cotyledon restraint. Finally, electronically viewing the embryo is simpler without liquid in the path of viewing.

Thus, a method of delivering plant embryos in a manufactured seed formed in accordance with the present invention has a high degree of reliability, and is able to mass produce manufactured seeds or deliver embryos in a given orientation in a plate, greenhouse container or other seed designs. Further such a method for delivering plant embryos also minimizes the risk of damaging or contaminating the plant embryo during the process of manufacturing the seed.

BRIEF DESCRIPTION OF THE DRAWINGS

The foregoing aspects and many of the attendant advantages of this invention will become better understood by reference to the following detailed description, when taken in conjunction with the accompanying drawings, wherein.

DETAILED DESCRIPTION OF THE PREFERRED EMBODIMENT

Figure 1:
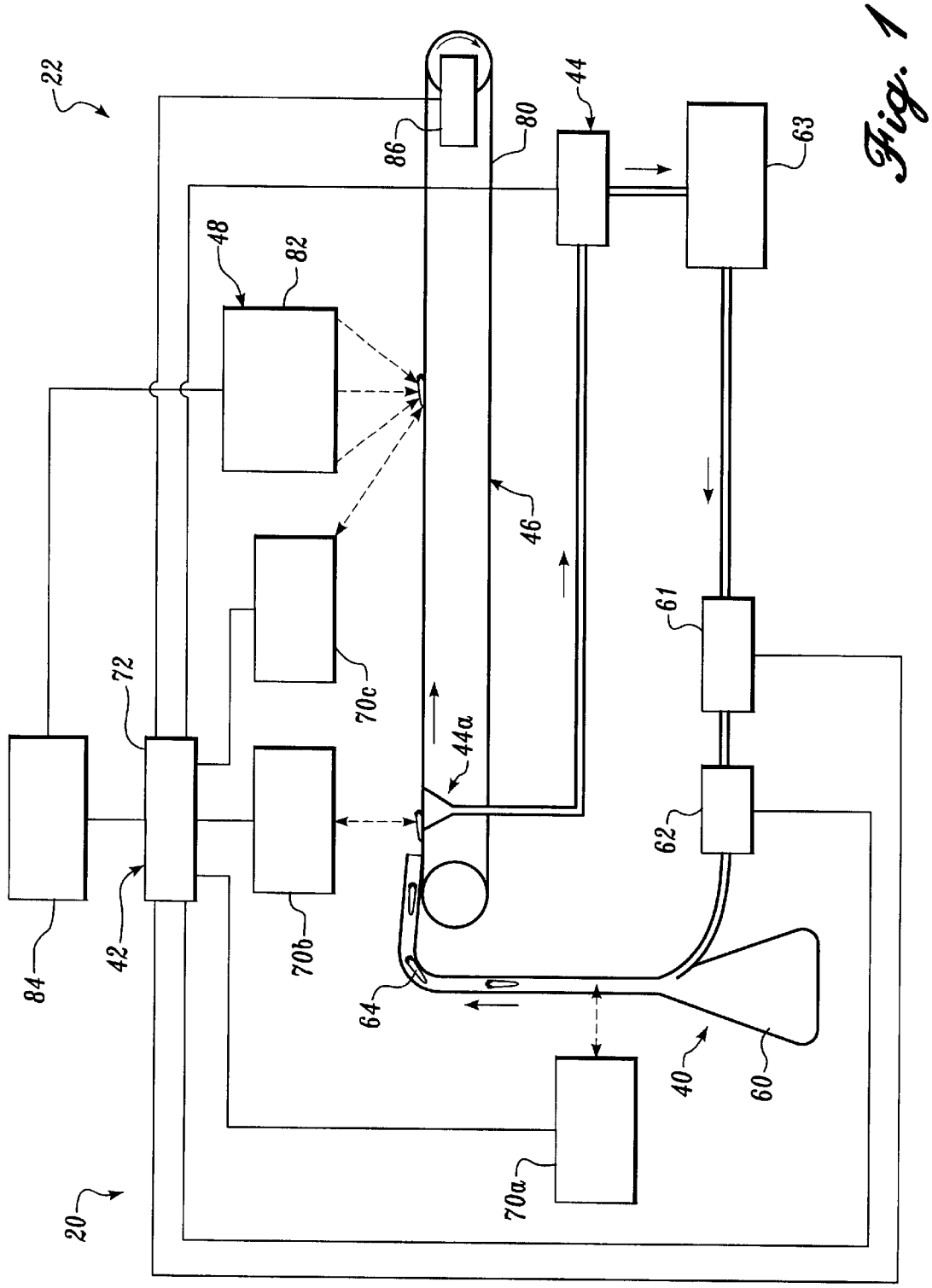
FIG. 1 is a partial schematic view of an embryo delivery system formed in accordance with one embodiment of the present invention.
Figure 2:
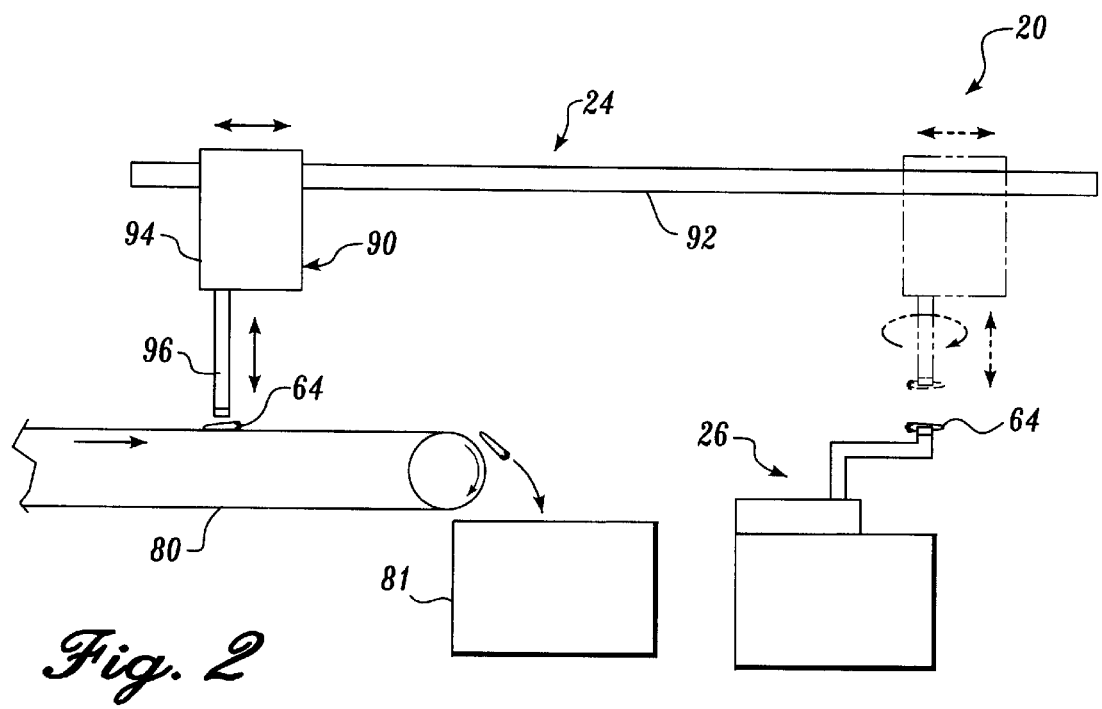
FIG. 2 is a partial side planar view showing a first robotic arm and conveyer belt for an embryo delivery system formed in accordance with one embodiment of the present invention.
Figure 3:
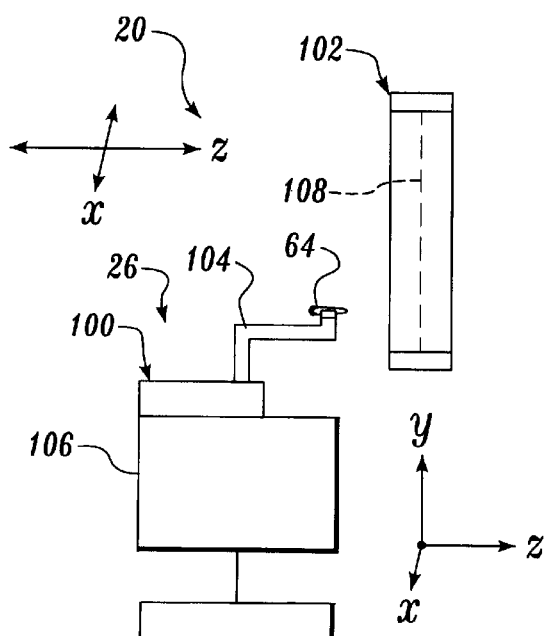
FIG. 3 is a partial side view of a measurement assembly for an embryo delivery system formed in accordance with one embodiment of the present invention shown in non-measuring position.
Figure 4:
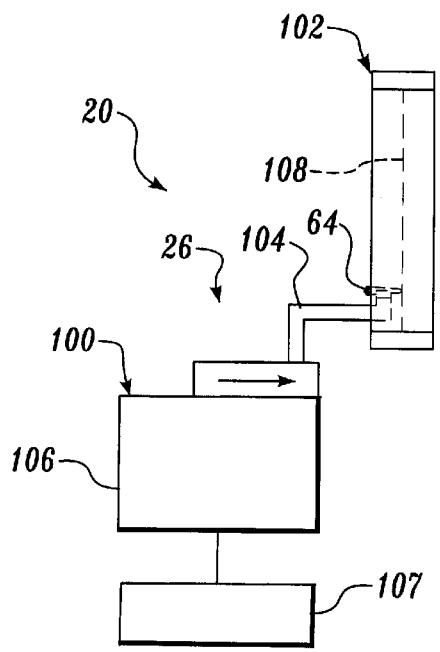
FIG. 4 is a partial side view of a measurement assembly for an embryo delivery system formed in accordance with one embodiment of the present invention shown in a measuring position.

FIGS. 1–6 illustrate a preferred embodiment of an embryo delivery system (EDS) 20 constructed in accordance with the present invention. For ease of illustration and clarity, various components of the EDS 20 are broken into FIGS. 1–6. One embodiment of the EDS 20 includes four major stages of delivery. The first stage includes an embryo orientation and imaging system 22 (FIG. 1). The second stage includes a first transfer assembly 24 (FIG. 2). The third stage includes an embryo measurement assembly 26 (FIGS. 3 and 4). The fourth stage includes an embryo placement assembly 28 (FIGS. 5–8) and a two-dimensional positioning table 30 (FIG. 2).

As may be best seen by referring to FIG. 1, the embryo orientation and imaging system 22 includes an embryo orientation assembly 40, a controller assembly 42, a vacuum system 44, a conveyor system 46, and an imaging system 48. The embryo orientation assembly 40 may be a well known assembly, such as that disclosed in U.S. Pat. No. 5,284,765, issued to Bryan et al., the disclosure of which is hereby incorporated by reference. The embryo orientation assembly 40 includes a containment vessel 60 and a control valve 62 in communication with the controller assembly 42 to selectively regulate the output of plant embryos from the containment vessel 60. The containment vessel 60 is filled with a liquid and has a plurality of plant embryos 64 contained therein. Suitably, the plant embryos 64 placed in the containment vessel 60 are caused to float by adjusting the specific gravity of the liquid within the containment vessel 60 to be higher than the specific gravity of the embryos 64 by a predetermined amount. Floating embryos have been found to sustain a higher percentage of acceptable or qualified embryos for implantation in a manufactured seed coat, as is described in greater detail below.

The controller assembly 42 includes detectors 70a–70c and a controller 72. The first detector 70a is suitably a well known photoelectric sensor. Other sensors, such as optical or infrared, are also within the scope of the invention. The first detector 70a is disposed adjacent the top of the containment vessel 60. The controller 72 polls the first detector 70a to determine when an embryo or embryos 64 have floated to the top of the containment vessel 60. When the controller 72 determines that the first detector 70a has detected an embryo 64, the controller 72 activates a solenoid (not shown). The solenoid in turn actuates a pump 61, connected to a reservoir 63, and a valve 62 that permits liquid to flow in at the top of the containment vessel 60 to direct the embryo 64 into the tube which will transport the embryo out of the containment vessel 60 and onto the conveyor system 46. This stream of liquid forces the embryo 64 into the tube toward the conveyor system 46.

The second detector 70b is located adjacent the end of the tube of the containment vessel 60. When the controller 72 determines that the second detector 70b has detected a passing embryo 64, it activates a well known conveyor drive motor 86 of the conveyor system 46, such that an embryo 64 is transferred to the conveyor system 46 without disturbing the orientation as it is ejected from the containment vessel 60. The second detector 70b is in communication with the controller 72 and may be adjusted to control the number and frequency in which plant embryos 64 are released from the containment vessel 60.

Still referring to FIG. 1, plant embryos 64 are ejected from the containment vessel 60 in a predetermined orientation. Suitably, each plant embryo 64 is emitted from the containment vessel 60, such that the embryos 64 come out of the containment vessel 60 cotyledon end first. Although orientating plant embryos such that they are emitted cotyledon end first is preferred, other orientations, such as emitting plant embryos 64 root end first, are also within the scope of the present invention. The plant embryos 64 are ejected onto the conveyor system 46 and transported to the imaging system 48.

The conveyor system 46 includes a well known continuous and liquid porous conveyor belt 80 and is driven by a motor 86. The vacuum system 44 is suitably disposed near the outlet of the containment vessel 60, such that when the plant embryos 64 are emitted from the containment vessel 60, they are vacuumed to remove additional or excess liquid on the plant embryos 64. The vacuum system 44 vacuums excess liquid from the plant embryos 64 through the porous conveyor belt 80. Although it is preferred that the vacuum process occur at a single location, additional locations, such as continuously vacuuming the plant embryo as it is being transferred to the imaging system, are also within the scope of the present invention.

After the plant embryos 64 have been subjected to the vacuum system 44, the conveyor system 46 is activated to transfer the plant embryos 64 to the imaging system 48. A third detector 70c is disposed near the imaging system 48. When the controller 72 determines from polling that the third detector 70c has detected an embryo 64, it signals the conveyor drive motor 86 to turn off, thereby positioning the embryo 64 in a suitable location for imaging by the imaging system 48.

The imaging system 48 includes an imaging camera 82, such as a digital camera, and a well known detector sensor (not shown). As the plant embryo 64 is transferred into the range of the detector sensor, the detector sensor sends a signal to the main computer 84. The main computer 84, in turn, sends a signal to the controller 72 to stop the conveyor belt 80, thereby positioning the plant embryo 64 beneath the digital camera 82. The camera 82 acquires and digitally stores images that will be used to determine whether an embryo is considered qualified to be placed in a manufactured seed.

Information from the imaging camera 82 is sent to the main computer 84 and is processed by a software program, such as that disclosed in PCT Application Serial No. PCT/US99/12128, entitled: Method for Classification of Somatic Embryos, filed Jun. 1, 1999, the disclosure of which is hereby expressly incorporated by reference. The software program makes a qualitative determination of the plant embryo 64 and, based on predetermined parameters, defines and stores which plant embryos are considered to be qualified and which are considered to be unqualified embryos.

Referring to FIG. 2, the first transfer assembly 24 will now be described in greater detail. The first transfer assembly 24 includes a robotic arm assembly 90 movably attached to a rail 92. The robotic arm assembly 90 includes a housing 94 and an arm 96. The lower end of the arm 96 includes a vacuum tip end adapted to selectively seize a plant embryo 64. As a non-limiting example, if a plant embryo 64 is deemed to be qualified by the software program to be placed into a manufactured seed, it is plucked off the conveyor belt 80 by the vacuum tip end of the robotic arm 96. The vacuum tip seizes the middle section of the plant embryo 64 and transfers the qualified plant embryo to the embryo measurement assembly 26. Unqualified plant embryos are rejected off the end of the conveyor into a trash receptacle 81. Although the preferred actuation for the robotic arm assemblies has movement in two axes, movement in more than two axes, such as a three axes system, is also within the scope of the present invention.

Figure 5:
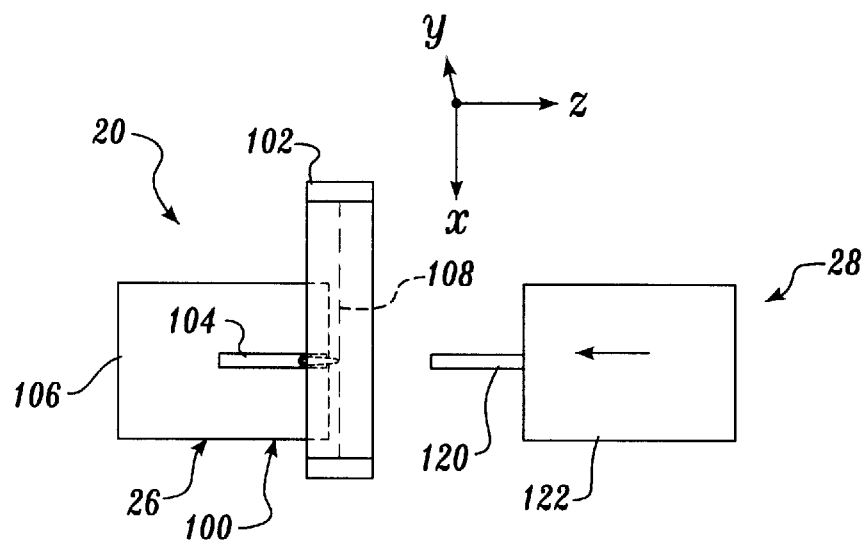
FIG. 5 is a partial top planar view of the measurement assembly shown in FIGS. 3 and 4 with the measuring assembly shown in a measuring position.

Referring to FIGS. 3 through 5, the embryo measurement assembly 26 includes a precision robotic arm embryo holder assembly 100 and a first laser micrometer 102. Preferably, the precision robotic arm embryo holder assembly 100 has motion in two axes, wherein the first axis is into a laser micrometer measurement plane 108, and as indicated by the Z-direction of FIGS. 3 and 4. The second axis of motion is horizontally perpendicular to the measurement plane 108, and as indicated by the X-direction of FIG. 5.

The precision robotic arm embryo holder assembly 100 includes a vacuum activated embryo holder assembly 104 and is adapted to releasably receive the plant embryo 64 from the first robotic arm 96 (FIG. 2). During operation, after receiving the plant embryo 64 from the first robotic arm 96, the embryo holder assembly 104 slides along the housing 106 coupled to a frame 107 to move the tip of the root end of the plant embryo 64 into the well known two-dimensional laser micrometer measurement plane 108 emitted from the laser micrometer 102. A set of XYZ positional measurements is collected about the tip of the root end of the plant embryo 64. The set of XY positional information is recovered from the laser micrometer and the Z position is recovered from the known distance of the embryo measurement assembly 26 relative to the laser micrometer measurement plane 108. The XY positional measurement of the tip of the root end of the plant embryo 64 permits the plant embryo 64 to be precisely transferred to the embryo placement assembly 28.

Referring now to FIGS. 5–9, the embryo placement assembly 28 will now be described in greater detail. As may be best seen by referring to FIG. 9, the embryo placement assembly 28 includes a third robotic arm embryo holder 120, a housing 122, and a rail 124. The housing 122 is pivotally attached to the rail 124 by a pivot and slide assembly 126. Referring back to FIG. 5, after the XYZ positional measurements of the tip end of the plant embryo 64 are determined, the plant embryo 64 is transferred from the embryo measuring assembly 26, held in place by the embryo holder assembly 104, and precisely into the third robotic arm embryo holder 120. In this position, the plant embryo 64 is held in a predetermined position by the embryo holder 104.

Figure 6:
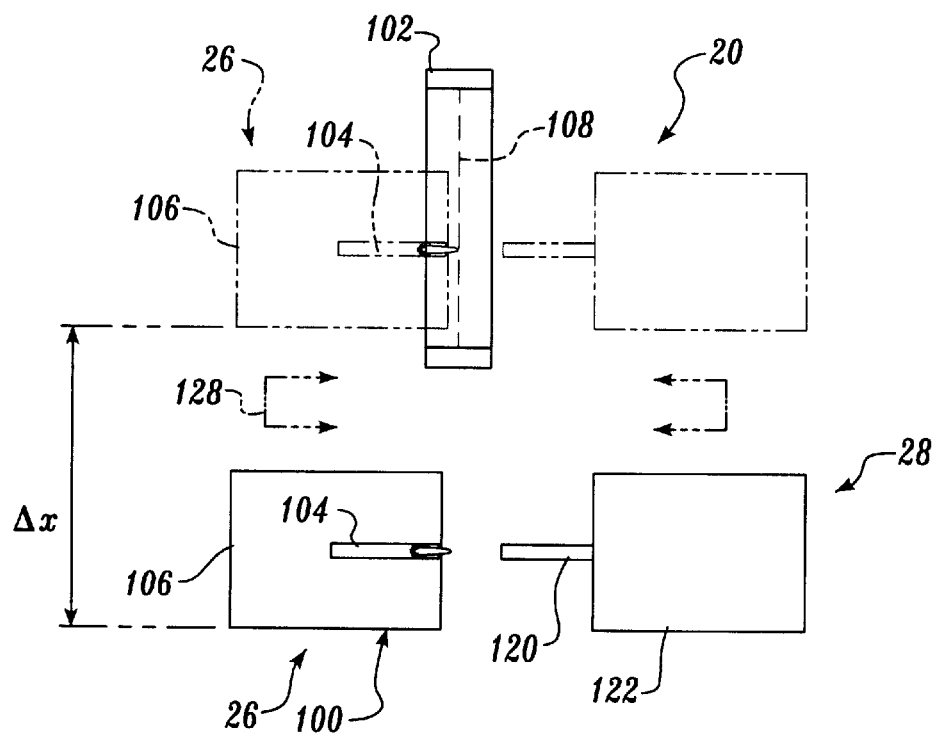
FIG. 6 is a partial top planar view of the measurement assembly shown in FIGS. 3 and 4 with the measurement assembly shown in both a measuring position and a transfer position.
Figure 7:
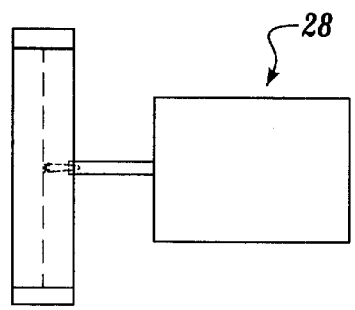
FIG. 7 is a partial top view of a second robotic arm for an embryo delivery system formed in accordance with one embodiment of the present invention showing measurements of a plant embryo.

The third robotic arm embryo holder 120, attached to the housing 122 by the rail 124, is moved, using information received about the position of the tip of the root end of the plant embryo 64 into a position where the cavity 130 of the third robotic arm embryo holder 120 is placed over the tip of the root end of the plant embryo 64. The vacuum is activated to pick up the embryo and deactivated to the embryo holder, thereby transferring holding control of the plant embryo 64 from the embryo measurement assembly 26 to the embryo placement assembly 28. In this position, the precision robotic arm embryo holder assembly 100 translates away from the laser micrometer 102 to a known stop position and in the direction indicated by the arrow 128 (FIG. 6). In this precise stop position, the plant embryo 64 is transferred from the embryo holder assembly 104 to the third robotic arm embryo holder 120 of the embryo placement assembly 28.

Figure 8:
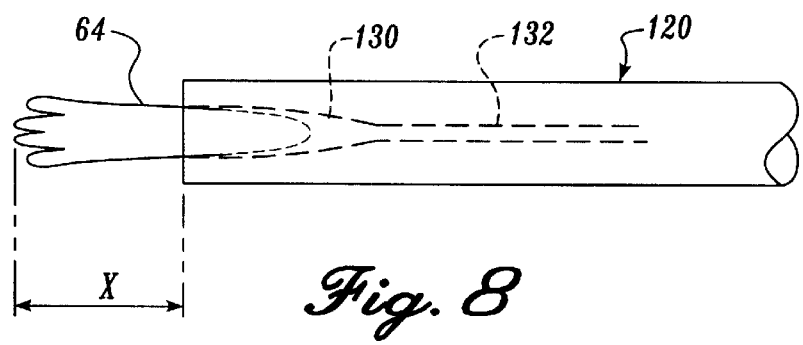
FIG. 8 is an enlarged view of a plant embryo received within a tip of the second robotic arm shown in FIG. 7.

As may be best seen by referring to FIG. 8, the end of the third robotic arm embryo holder 120 includes a conical cavity 130 in communication with a vacuum tube 132. When the plant embryo 64 is transferred from the embryo measuring assembly 26 to the embryo placement assembly 28, the root end of the plant embryo 64 is received within the conical tip cavity 130 and is held therein by the vacuum tube 132. In this position, the third robotic arm embryo holder 120, attached to the housing 122 and slide assembly 126, is moved away from the laser micrometer measurement plane 10 until the plant embryo 64 is moved totally out of the laser micrometer measurement plane 108. In this position, the cotyledon end of the plant embryo 64 protrudes out of the assembly 120.

As received within the third robotic arm embryo holder 120, the embryo placement assembly 28 translates back towards the laser micrometer 102. The precision measurement of the center of the cotyledon end of the plant embryo 64 is calculated and the length of the protrusion, indicated by the distance X, of the cotyledon end from the end of the third robotic arm embryo holder 120 is also calculated. The circumference of the cotyledon end is a standard measurement obtained from the well known laser micrometer. The center of the cotyledon end of the plant embryo 64 can be precisely calculated from that measurement.

Figure 9:
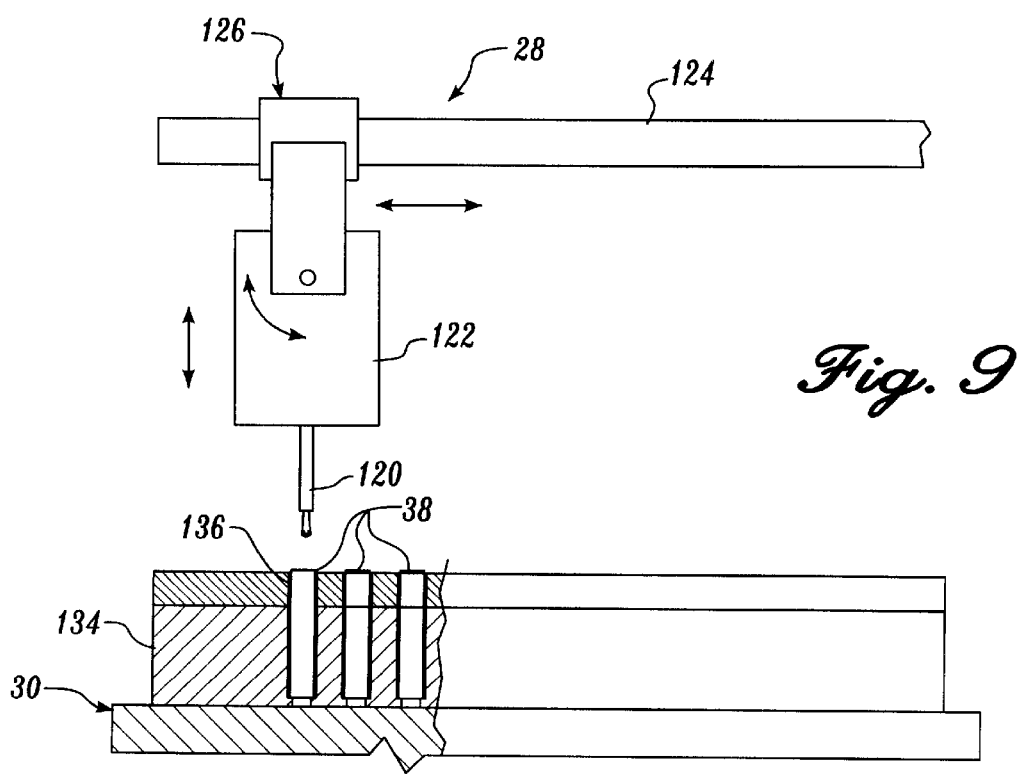
FIG. 9 is a partial side planar view of the second robotic arm for an embryo delivery system formed in accordance with one embodiment of the present invention showing rotation of the robotic arm to deposit the plant embryo within a seed coat.
Figure 10:
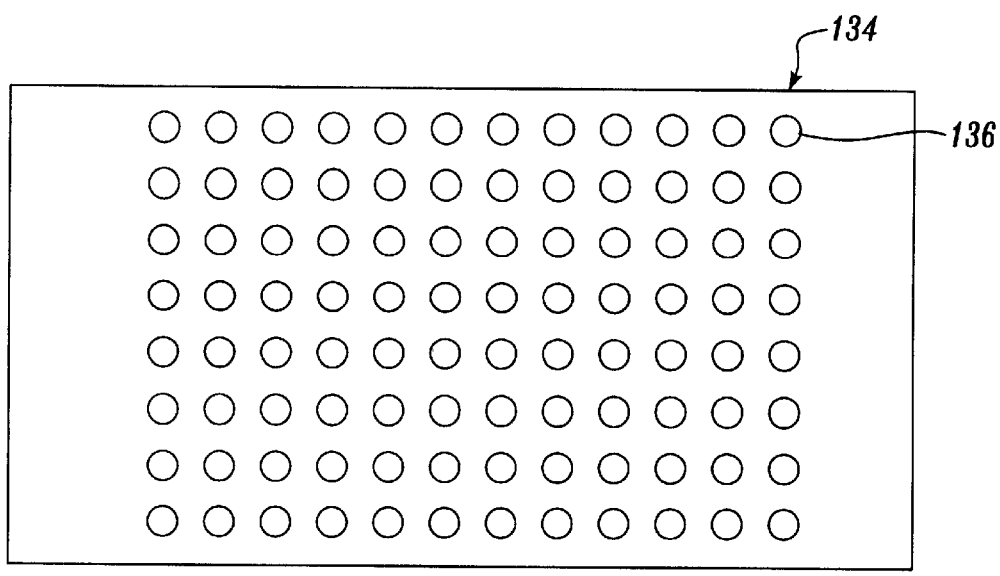
FIG. 10 is a top planar view of a tray receptacle for an embryo delivery system formed in accordance with one embodiment of the present invention.
Figure 11:
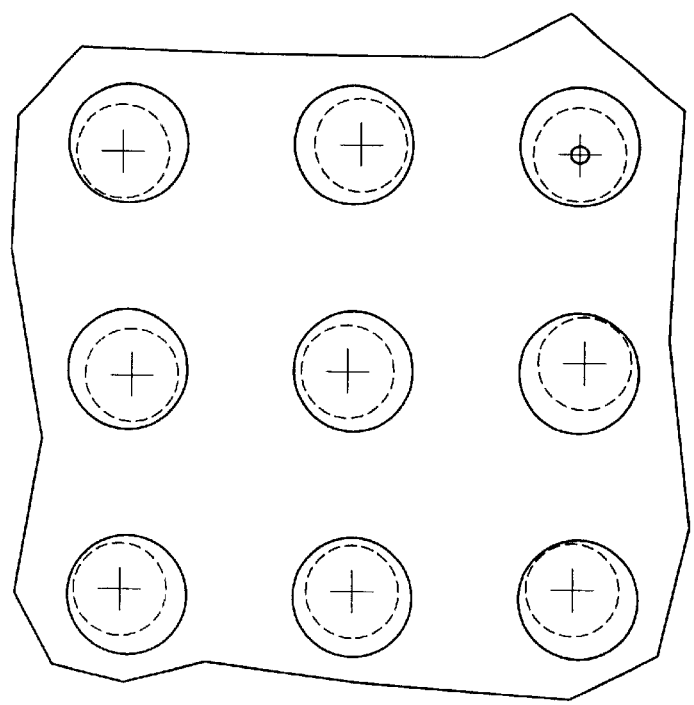
FIG. 11 is an enlarged view of a portion of the receptacle tray for an embryo delivery system formed in accordance with one embodiment of the present invention.

As may be best seen by referring to FIG. 9, after the center and length of the cotyledon end of the plant embryo 64 is determined, the housing 122 and third robotic arm embryo holder 120 pivot downwardly towards the two-dimensional positioning table 30. The two-dimensional positioning table 30 selectively translates in two dimensions. In particular, the table 30 is permitted to move fore and aft, as well as in the lateral direction. Although a two-dimensional table is preferred, a table capable of movement in other directions, such as a three-dimensional table, is also within the scope of the present invention.

Located on top of the table 30 is a receptacle tray 134. The receptacle tray 134 includes a plurality of cavities 136 extending vertically therethrough. Suitably, there may be a total of 96 cavities located in the receptacle tray 134. However, a receptacle tray 134 having more or less cavities is also within the scope of the present invention.

Received within each cavity 136 is a well known manufactured seed 38, such as that disclosed in U.S. Pat. No. 5,701,699, issued to Carlson et al., the disclosure of which is hereby incorporated by reference. The two-dimensional positioning table 30 includes an imaging camera (not shown) to precisely locate and store the center of the opening of the cotyledon restraint in the manufactured seed. Having the positional information of the cotyledon restraint opening of the manufactured seed and the position information of the cotyledon end of the embryo 64 held by the vacuum tip of the third robotic arm embryo holder 120, the third robotic arm embryo holder 120 positions the embryo 64 above the cotyledon restraint opening of the manufactured seed. The third robotic arm embryo holder 120 positions the embryo 64 above the opening of the cotyledon restraint and lowers the embryo 64 therein to a predetermined depth within the opening and above the bottom of the opening. At this point, the vacuum tip is turned off and a short burst of air gently releases the embryo 64 from the vacuum tip 120 and into the cotyledon restraint of the manufactured seed.

Operation of the EDS may be best understood by referring to FIGS. 1–11. After the embryo 64 is delivered from the manufactured seed production line, the embryo 64 is placed in the containment vessel 60 of the embryo orientation assembly 40. As noted above, the embryos are placed within the containment vessel 60 to segregate the floating from non-floating embryos 64. The plant embryos are caused to float to the top of the container, such that the plant embryo floats upwardly within the container cotyledon end first. From the top of the container, additional liquid is used to propel the plant embryos out of the container while maintaining their cotyledon end first orientation.

As the embryos are detected exiting the delivery tube, the detector 70 causes the controller 72 to start the porous conveyor belt 80 moving such that the embryos 64 will be placed on the conveyor belt 80 at close or at the same speed at which they are exiting the delivery tube. This ensures that the embryos 64 will be placed on the conveyor belt 80 and maintain their orientation, rather than dropped on the belt 80 and randomly lose their orientation as they bounce to settle on the belt 80. Simultaneously, the vacuum 44 starts and the vacuum nozzle located beneath the conveyor belt 80 vacuums off any excess liquid around the plant embryo that has drained on the porous belt 80 and seeped to below the belt 80.

Moving on the conveyor belt 80, the embryo 64 is again detected by a well known photoelectric detector and the conveyor belt 80 is stopped by the controller 42 in the correct position for the imaging camera 82. The imaging camera 82 acquires and digitally stores the necessary images that will be used to determine whether the embryo 64 can be considered qualified to be placed in a manufactured seed.

If the embryo 64 is qualified to be placed in a manufactured seed, it is plucked off the conveyor belt 80 by the vacuum tip located at the end of the first arm 96. The vacuum tip picks up the embryo 64 from the middle section of the embryo 64, places the embryo 64 on a second vacuum tip of the embryo placement measurement 26. The embryo holder assembly 104 holds the lower surface of the embryo 64, with the root end protruding sideways from the vacuum tip. The vacuum tip is fastened to a two-axes motion control table that will move the tip of the embryo 64 into a two-dimensional laser micrometer field 108, thereby calculating a set of XYZ positional measurements about the root end of the embryo 64. The set of XY position information is recovered from the laser micrometer 102 and the Z position is recovered from the precision motion of the controlled table controller.

Having the three-dimension position information for the tip of the root end of the embryo 64, the precision motion control table controller moves the tip to a position that will allow the root end of the embryo 64 to be placed precisely into the opening of another vacuum tip of the embryo placement assembly 28. The embryo 64 held by the third robotic arm embryo holder 120 then moves back into the laser micrometer 102, where the position measurement of the center of the cotyledon end of the embryo 64 is calculated and the length of the protrusion of the cotyledon end from the end of the vacuum tip is also calculated.

As noted above, simultaneous with or prior to the acquisition of the precision information for the embryo, a second imaging system such as OMRON Vision Systems Model F350, F300 or F200, locates the position of the opening of the cotyledon restraint in the manufactured seed secured to the two-dimensional positioning table 30. As a result, having both the positional information of the cotyledon restraint opening of the manufactured seed and the position information of the cotyledon end of the embryo, the third robotic arm embryo holder 120 positions the embryo above the cotyledon restraint opening and precisely lowers the embryo 64 within the cotyledon restraint.

The previously described version of the present invention provides several advantages over currently available embryo delivery systems. First, the overall system is simpler and more reliable than the liquid-based systems currently available by using a combination of robotics, computers, vision systems, motion controlled components, laser micrometers and other basic electronics. Further, the embryos may be accurately placed into the cotyledon restraint without damaging or contaminating the embryos. Thus, a method and apparatus of delivering plant embryos in a manufactured seed formed in accordance with the present invention has a high degree of reliability, is able to mass produce manufactured seeds and minimize the risk of damaging or contaminating the plant embryo during the process of manufacturing the seed.

From the foregoing description, it can be seen that an embryo delivery system formed in accordance with the present invention incorporates many novel features and offers significant advantages over currently available systems. While the presently preferred embodiments of the invention have been illustrated and described, it is to be understood that within the scope of the appended claims, various changes can be made therein without departing from the spirit of the invention.

The embodiments of the invention in which an exclusive property or privilege is claimed are defined as follows:

1. A method of inserting a plant embryo into a manufactured seed coat, the method comprising the steps of:
    (a) selecting qualified plant embryos from a plurality of plant embryos, wherein the step of selecting qualified plant embryos from a plurality of plant embryos includes the step of analyzing the plurality of plant embryos according to a predetermined quality criteria to identify qualified plant embryos;
    (b) positioning a seed coat relative to at least one of the qualified plant embryos;
    (c) obtaining three-dimensional measures of the qualified plant embryo; and
    (d) depositing the at least one of the qualified plant embryos in the seed coat according to the three-dimensional measures.

2. The method of claim 1, further comprising the step of acquiring images of the plurality of plant embryos to analyze each of the plurality of plant embryos according to a predetermined quality criteria to identify qualified plant embryos.

3. The method of claim 1, further comprising the step of orientating the plurality of plant embryos in a predetermined position.

4. The method of claim 1, further comprising the step of orientating the plurality of plant embryos in a predetermined position within a container of fluid.

5. The method of claim 4, further comprising the step of expelling each of the plurality of plant embryos from the container.

6. The method of claim 5, further comprising the step of determining a speed at which each of the plurality of plant embryos are expelled from the container.

7. The method of claim 6, further comprising the step of transporting each of the plurality of plant embryos at substantially the same speed as each of the plurality of plant embryos are expelled from the container.

8. The method of claim 7, wherein the step of transporting each of the plurality of plant embryos includes the step of controllably actuating a conveyor belt to place each of the plurality of plant embryos on the conveyor belt at substantially the same speed as each of the plurality of plant embryos are removed from the container to maintain the predetermined position of each of the plurality of plant embryos.

9. The method of claim 7, further comprising the step of removing excess fluid from each of the plurality of plant embryos.

10. The method of claim 9, wherein the step of removing excess fluid from each of the plurality of plant embryos includes the step of vacuuming each of the plurality of plant embryos.

11. The method of claim 10, further comprising the step of acquiring images of the plurality of plant embryos to analyze each of the plurality of plant embryos according to a predetermined quality criteria to identify qualified plant embryos.

12. The method of claim 11, further comprising the step of transferring each qualified plant embryo from a first location to a second location.

13. The method of claim 12, wherein the step of transferring each qualified plant embryo includes a vacuum tip transfer assembly, the vacuum tip transfer assembly controllably transferring the qualified plant embryo to the second location.

14. The method of claim 12, further comprising the step of measuring each qualified plant embryo.

15. The method of claim 14, wherein the step of measuring each qualified plant embryo includes a laser micrometer to calculate three-dimensional measurements of one end of the qualified plant embryo.

16. The method of claim 1, further comprising the step of controllably transferring the qualified plant embryo from the second location to a third location.

17. The method of claim 16, wherein the step of controllably transferring the qualified plant embryo from the second location to a third location includes a second vacuum tip transfer assembly.

18. The method of claim 17, further comprising the step of measuring one end of the qualified plant embryo to determine a center of the one end of the qualified plant embryo.

19. The method of claim 17, further comprising the step of locating an opening of a tray having a plurality of openings.

20. The method of claim 19, wherein the tray includes a manufactured seed coat within each opening.

21. The method of claim 20, further comprising the step of controllably inserting the qualified plant embryo in the manufactured seed coat.

22. A method of delivering cultivated plant embryos to a growing medium, the method comprising the steps of:
    (a) orientating a plurality of plant embryos in a predetermined orientation;
    (b) analyzing each of the plurality of plant embryos according to a predetermined quality criteria to identify qualified plant embryos;
    (c) measuring one end of the qualified plant embryos to determine three-dimensional positional measurements of the one end of a qualified plant embryo; and
    (d) inserting each qualified plant embryo in a growing medium according to the three-dimensional positional measurements.

23. The method of claim 22, further comprising the step of acquiring images of the plurality of plant embryos to analyze each of the plurality of plant embryos according to a predetermined quality criteria to identify qualified plant embryos.

24. The method of claim 22, further comprising the steps of removing the plurality of plant embryos from a container of fluid and determining a speed at which the plant embryos are removed from the container.

25. The method of claim 24, further comprising the step of transporting each of the plurality of plant embryos at substantially the same speed as each of the plurality of plant embryos are removed from the container.

26. The method of claim 25, further comprising the step of vacuuming each of the plurality of plant embryos to remove excess fluid from each of the plurality of plant embryos.

27. The method of claim 26, further comprising the step of transferring each qualified plant embryo from a first location to a second location.

28. The method of claim 27, wherein the step of transferring each qualified plant embryo includes a vacuum tip transfer assembly, the vacuum tip transfer assembly controllably transferring the qualified plant embryo to the second location.

29. The method of claim 28, further comprising the step of controllably transferring the qualified plant embryo from the second location to a third location.

30. The method of claim 29, wherein the step of controllably transferring the qualified plant embryo from the second location to a third location includes a vacuum tip transfer assembly.

31. The method of claim 30, further comprising the step of measuring one end of the qualified plant embryo to determine a center of the one end of the qualified plant embryo.

32. The method of claim 31, further comprising the step of locating an opening of a tray having a plurality of openings.

33. The method of claim 32, wherein the tray includes a manufactured seed coat within each opening.

34. The method of claim 33, further comprising the step of controllably inserting the qualified plant embryo in the manufactured seed coat.

35. A method of delivering cultivated embryos comprising the steps of:

(a) orientating a plurality of embryos in a predetermined orientation;

(b) analyzing each of the plurality of embryos according a predetermined quality criteria to identify qualified embryos;

(c) determining three-dimensional positional measurements of the qualified embryos;

(d) positioning a first seed coat relative to the qualified embryos; and (e) inserting one of the qualified embryos in the seed coat according to the three-dimensional positional measurements of the qualified embryos to minimize damage to and contamination of the qualified embryos.

36. The method of claim 35, further comprising the step of acquiring images of the plurality of plant embryos to analyze each of the plurality of plant embryos according to a predetermined quality criteria to identify qualified plant embryos.

37. The method of claim 36, further comprising the step of transferring each qualified plant embryo from a first location to a second location.

38. The method of claim 37, wherein the step of transferring each qualified plant embryo includes a vacuum tip transfer assembly, the vacuum tip transfer assembly controllably transferring the qualified plant embryo to the second location.

39. The method of claim 37, further comprising the step of measuring each qualified plant embryo.

40. The method of claim 39, wherein the step of measuring each qualified plant embryo includes a laser micrometer to calculate three-dimensional measurements of one end of the qualified plant embryo.

41. The method of claim 40, further comprising the step of controllably transferring the qualified plant embryo from the second location to a third location.

42. The method of claim 41, wherein the step of controllably transferring the qualified plant embryo from the second location to a third location includes a second vacuum tip transfer assembly.

43. The method of claim 41, further comprising the step of measuring one end of the qualified plant embryo to determine a center of the one end of the qualified plant embryo.

44. The method of claim 43, further comprising the step of locating an opening of a tray having a plurality of openings.

45. The method of claim 44, wherein the tray includes a manufactured seed coat within each opening.

46. The method of claim 45, further comprising the step of controllably inserting the qualified plant embryo in the manufactured seed coat.

* * * * *